United States Patent
Agar et al.

(10) Patent No.: US 8,881,577 B1
(45) Date of Patent: Nov. 11, 2014

(54) METHOD AND SYSTEM FOR ANALYSIS OF RHEOLOGICAL PROPERTIES AND COMPOSITION OF MULTI-COMPONENT FLUIDS

(71) Applicant: Agar Corporation, Ltd., George Town (KY)

(72) Inventors: Joram Agar, George Town (KY); David Farchy, Houston, TX (US)

(73) Assignee: Agar Corporation, Ltd., Georgetown (KY)

( * ) Notice: Subject to any disclaimer, the term of this patent is extended or adjusted under 35 U.S.C. 154(b) by 0 days.

(21) Appl. No.: 13/840,765

(22) Filed: Mar. 15, 2013

Related U.S. Application Data

(60) Provisional application No. 61/619,156, filed on Apr. 2, 2012.

(51) Int. Cl.
G01N 11/08 (2006.01)
G01N 35/00 (2006.01)

(52) U.S. Cl.
CPC .............................. *G01N 35/00584* (2013.01)
USPC ........................................................ 73/54.06

(58) Field of Classification Search
CPC ......... G01N 9/32; G01N 11/06; G01N 11/08; G01N 11/04
See application file for complete search history.

(56) References Cited

U.S. PATENT DOCUMENTS

| | | | |
|---|---|---|---|
| 3,766,773 A | 10/1973 | Limpert | |
| 3,808,877 A * | 5/1974 | Blair | 73/54.06 |
| 3,908,442 A | 9/1975 | Chmiel | |
| 4,316,383 A | 2/1982 | Fruman et al. | |
| 4,574,622 A | 3/1986 | Hatfield | |
| 4,904,603 A | 2/1990 | Jones et al. | |
| 4,932,242 A * | 6/1990 | Kawashima et al. | 73/54.07 |
| 5,073,756 A | 12/1991 | Brandelik | |
| 5,306,909 A | 4/1994 | Jones et al. | |
| 5,360,738 A | 11/1994 | Jones et al. | |
| 5,519,214 A | 5/1996 | Houwen et al. | |
| 5,557,103 A | 9/1996 | Hughes et al. | |
| 6,009,747 A | 1/2000 | dos Santos | |
| 6,575,019 B1 * | 6/2003 | Larson | 73/54.04 |
| 6,707,556 B2 | 3/2004 | Turner et al. | |
| 7,251,565 B2 | 7/2007 | Storm, Jr. et al. | |
| 7,832,257 B2 | 11/2010 | Weightman | |
| 2005/0221495 A1 | 10/2005 | Bell et al. | |
| 2008/0245960 A1 | 10/2008 | Csutak | |
| 2010/0250142 A1 | 9/2010 | Zamora et al. | |

FOREIGN PATENT DOCUMENTS

EP 0065831 12/1982

* cited by examiner

*Primary Examiner* — Paul West
(74) *Attorney, Agent, or Firm* — Andrew W. Chu; Craft Chu PLLC

(57) ABSTRACT

A method and system for on-line multi-component fluid analysis, the system can be configured to measure the absolute viscosity using data acquired by monitoring the time it takes for a pump to move from one side to the other side and pressure at the discharge for a reference fluid and the time it takes for a pump to move from one side to the other side and pressure at the discharge for a sample fluid. The system and method can also include comparing the data acquired for the sample fluid and the reference fluid. The system and method can present rheological behavior of the sample fluid as Newtonian viscosity and the shear rate in real time.

15 Claims, 7 Drawing Sheets

METHOD AND SYSTEM FOR ANALYSIS OF RHEOLOGICAL PROPERTIES AND COMPOSITION OF MULTI-COMPONENT FLUIDS

CROSS REFERENCE TO RELATED APPLICATION

The current application claims priority to and the benefit of U.S. Provisional Patent Application Ser. No. 61/619,156 filed Apr. 2, 2012, entitled "METHOD AND SYSTEM FOR RHEOLOGICAL PROPERTIES AND COMPOSITION OF MULTI-COMPONENT FLUIDS". This reference is incorporated in its entirety.

FIELD

The present embodiments generally relate to a method and system for on-line multi-component fluid analysis.

BACKGROUND

A need exists for an accurate and multi-functional method and measuring system that can perform the analysis of rheological properties and compositions of multi-component fluids in on-line condition, at wide ranges of fluid temperatures and pressures and simultaneous measurements of fluid components.

A further need exists for a system that is simple, fast, inexpensive, and has suitable dimensions and weight.

A further need exists for a method and system that provides real time on the spot analysis of fluid proportion such as fluid density, composition of hydrocarbon/solids and water, salt content, rheological curve, rheological hysteresis, density, temperature, electrical stability, Newtonian viscosity—$\tau$, Bingham Plastic Constant $\tau_y$, $\mu_p$, Power Law Constant K, m, Herschel-Bulkley Constant $\tau_y$, k, m, and other important properties essential in the drilling operation.

The present embodiments meet these needs.

BRIEF DESCRIPTION OF THE DRAWINGS

The detailed description will be better understood in conjunction with the accompanying drawings as follows.

Figure 1:
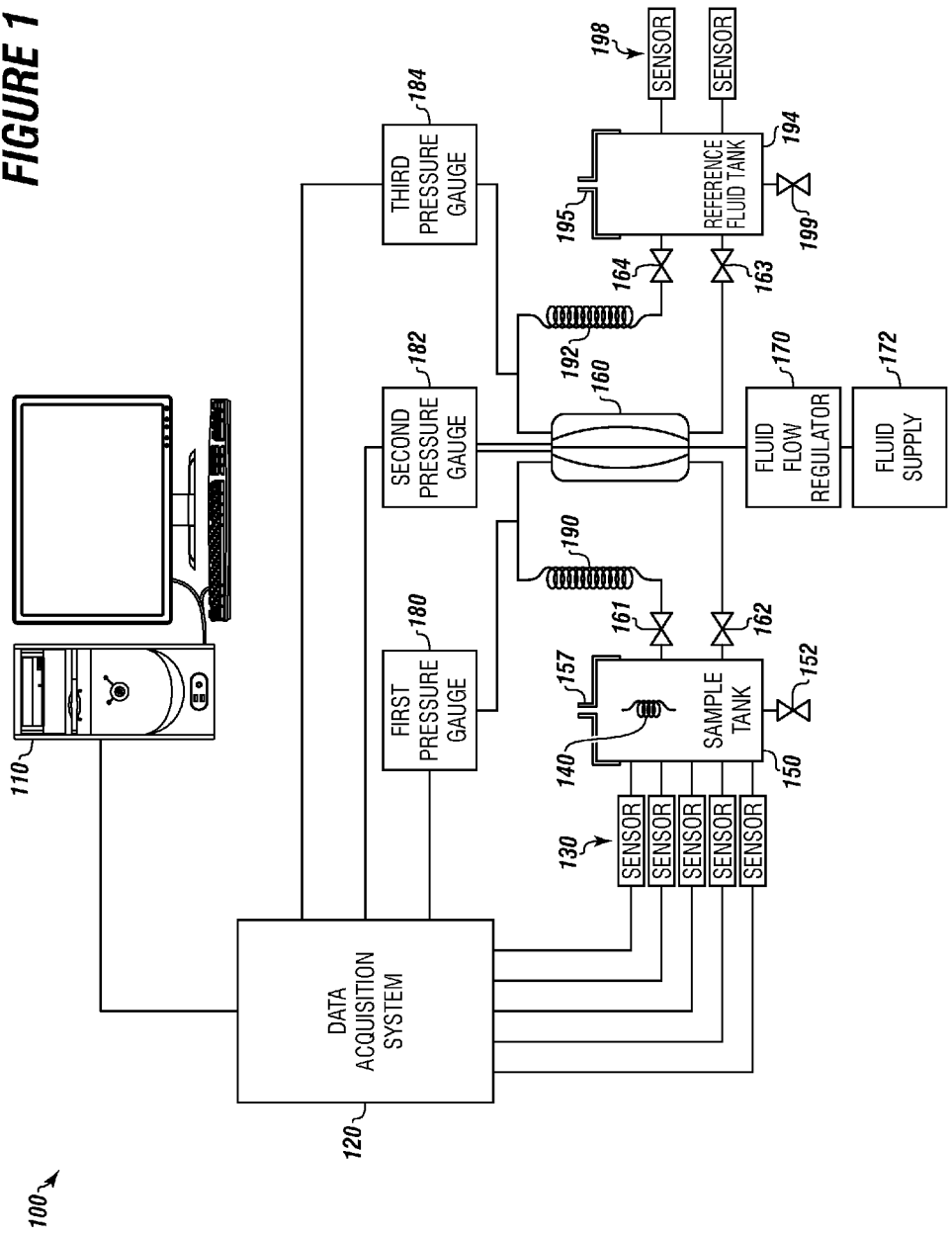
FIG. 1 depicts a schematic of a system when the sample fluid source is a sample tank.

The present embodiments are detailed below with reference to the listed Figures.

DETAILED DESCRIPTION OF THE EMBODIMENTS

Before explaining the present method and system in detail, it is to be understood that the method and system are not limited to the particular embodiments and that it can be practiced or carried out in various ways.

The present embodiments generally relate to a method and system for on-line multi-component fluid analysis.

The system can be configured to measure the absolute viscosity using data acquired by monitoring the time it takes for a pump to move from one side to the other side, i.e., reference fluid stroke time, and differential pressure for a reference fluid and the time it takes for a pump to move from one side to the other side, i.e., sample fluid stroke time, and differential pressure for a sample fluid. The sample fluid source can be a tank, a mud pit, a pipeline, or combinations thereof.

The data acquired for the sample fluid and the reference fluid can be compared. Comparing the acquired data can include comparing the sample fluid stroke time and the reference fluid stroke time and the differential pressure at the outlet of the pump for the reference fluid and the sample fluid.

For example the equation $\mu_s = \mu r^{(\tau_s P_s)}/(\tau_r P_r)$ can be used. $\mu_s$ is the measurement viscosity of the sample fluid; $\mu r$ is the viscosity of the reference fluid; $\mu_s$ is the sample fluid stroke time, $p_s$ is the differential pressure across the discharge lines for the sample fluid; $\tau_r$ is the reference fluid stroke time, $p_r$ is the pressure across the discharge lines for the reference fluid. By accounting for both the stroke time of both fluids and the pressure of both fluids a more accurate viscosity can be calculated for the sample fluid.

In one or more embodiments of a system for on-line multi-component fluid analysis, the system can include a first capillary tube in communication with a reference fluid source, and a second capillary tube in fluid communication with a sample fluid source. The capillary tubes can be any size. The capillary tubes can be sized to allow any size particles in the sample fluid to flow therethrough.

In one or more embodiments of the system, a temperature controller can be operatively connected with the sample fluid source. The temperature controller can be used to maintain the sample fluid at a constant temperature.

The capillary tubes can be in fluid communication with a pump. The pump can be a self-priming pump.

The system can also include a fluid supply in communication with the pump. The fluid supply can include an air source, a hydraulic fluid source, or the like.

The fluid supply can be in communication with a controllable fluid flow regulator. The controllable fluid flow regulator can be disposed between the pump and the fluid supply.

A first differential pressure gauge can be disposed between the inlet and the outlet of the first capillary tube, and a second differential pressure gauge can be disposed between the inlet and the outlet of the second capillary tube.

A data acquisition system can be in communication with the pump, air regulator, and the pressure gauges. The data acquisition system can be programmed to receive signals from one or more sensors or components of the system and manipulate the signals into a value for a parameter. For example, a thermocouple can send an electronic signal to the data acquisition system. The data acquisition system can receive the signal and relate the signal to a predetermined value.

The system can include a plurality of sensors in communication with the sample tank and the data acquisition system. The data acquisition system can use signals from the sensors to acquire property data on the sample fluid. The acquired property data can include a composition of hydrocarbon/solids and water, a salt content of sample fluid, a fluid density of the sample fluid, a density of the sample fluid, a temperature of the sample fluid, or an electrical stability of the sample fluid.

A computer can be in communication with the data acquisition system. The computer can be configured to control the fluid flow regulator and present rheological behavior of the fluid in terms of Newtonian viscosity and the shear rate in real time. The computer can be configured to determine composition of the sample fluid. For example, the computer can use optical methods, electrical methods, ph methods, or the like.

The computer can present the measured Newtonian viscosity versus shear rate by calculating the shear rate using the following: $\gamma = 8v/D = 2Q*\pi*D \ V/\tau_s$. $\gamma$ is the shear rate; $v$ is the velocity of the sample fluid through the capillary; D is the capillary diameter; Q is the flow rate; V is pump displacement; and $\tau_s$ is the sample fluid stroke time. Presenting data using this method provides better resolution of the bulk rheological behavior of the fluid flow through the capillary. The non-linearity of the cured and the non-Newtonian behavior is magnified for the sample fluid.

The computer can also present other information. For example, the computer can present a classic Rheogram for the non-Newtonian models. Shear can be calculated as $\tau = PD/4L$. $\tau$ is the shear stress, P is the differential pressure across the capillary, and L is the length of the capillary tube.

At the end of each test cycle calculation of the Rheological constant can be performed by the computer. The Rheological constants can be calculated using data acquired during the test cycle using preinstalled formulas or predefined constants stored in the data storage of the computer. The Rheological constant can be reported and include Newtonian viscosity—t; Bingham Plastic Constant, Power Law Constant, Herschel-Bulkley Constant Bingham Number, Blak Number, or combinations thereof. Using the Rheological Constant and additional inputs of the pipe and drilling geometry, standing pressure can be calculated using computer instructions in communication with the computer.

In one or more embodiments, a pressure chamber can be in communication with a first portion of the pipeline via a first conduit, and in fluid communication with a second portion of the pipeline via a second conduit. Flow through the first conduit can be controlled by a first flow valve, and flow through the second conduit can be controlled by a second flow valve. The pressure chamber can have a pressure relief valve configured to release pressure from the sample fluid in the pressure chamber. The pressure chamber can have an outlet in fluid communication with the pump.

In one or more embodiments, the system can include a purge system configured to allow purging of the system with sample fluid prior to running measurements.

The system can be used to perform a method for on-line multi-component fluid analysis. The method can include pumping a reference fluid through a first capillary tube using a pump, and pumping a sample fluid through a second capillary using the pump.

The method can also include controlling a fluid flow regulator while pumping the sample fluid and reference fluid through the capillary tubes.

Reference fluid data can be acquired by measuring the time it takes the pump to move from one side to the other side and monitoring the differential pressure across the reference capillary, and sample fluid data can be acquired by measuring the time it takes the pump to move from one side to the other side and monitoring the differential pressure at the across the capillary.

After the sample fluid data and reference fluid data is acquired, the sample fluid data and the reference fluid data can be compared to one another.

The method can also include determining and presenting the Newtonian viscosity and shear rate in real time.

In one or more embodiments, the method can include controlling the temperature of the sample fluid.

In one or more embodiments, the method can include communicating a first conduit with a pressure chamber and a first portion of a high pressure pipeline and a second conduit with the pressure chamber and a second portion of the high pressure pipeline. An outlet of the pressure chamber can be placed in communication with the pump. Flow through the first conduit and the second conduit can be allowed, and fluid flow out of the outlet can be prevented. This can allow a high pressure fluid sample to be obtained within the pressure chamber. After the high pressure fluid sample is collected, fluid flow through the first conduit and the second conduit can be prevented, and the pressure of the high pressure fluid sample in the pressure chamber can be reduced to a predetermined pressure, forming a fluid sample. The fluid sample can be allowed to flow out of the pressure chamber to the pump and capillary tubes for measurement.

Turning to the Figures, FIG. 1 depicts a schematic of the system when the sample fluid source is a sample tank.

The system 100 can include a computer 110, a data acquisition system 120, a sample tank 150, a pump 160, a controllable fluid flow regulator 170, a fluid supply 172, one or more pressure gauges, such as a first pressure gauge 180, a second pressure gauge 182, and a third pressure gauge 184, a first capillary tube 190, a second capillary tube 192, a reference fluid tank 194, one or more plurality of sensors, such as a second plurality of sensors 198 and first plurality of sensors 130.

The computer 110 can be any data processing system configured to receive acquired data from the data acquisition system 120, control one or more components of the system 100, and manipulate the data as described herein.

The data acquisition system 120 can be in communication with the computer 110. The data acquisition system 120 can be placed in communication with the computer 110 by any type of telemetry. Illustrative telemetry includes wired, wireless, or combinations thereof. The data acquisition system 120 can be integrated with the computer 110 or independent therefrom.

The first plurality of sensors 130 can be configured to monitor one or more properties of the sample fluid. The first plurality of sensors 130 can send signals to the data acquisition system 120. The data acquisition system 120 can acquire the signals and transform the signals into data, thereby acquiring data on the one or more properties of the sample fluid. The first plurality of sensors 130 can include multi-frequency dielectric measurement devices; temperature devices, such as thermo couples; conductivity measurement devices, electrical stability meters, and radiology meters, other sensors, or combinations thereof. The first plurality of sensors 130 can be in communication with the sample tank 150.

The heating element 140 can be any direct or indirect heat transfer device. For example the heating element 140 can be a coiled heating apparatus, a concentric tube heat exchanger, a counter flow heat exchanger, or other heat transfer devices.

The heating element 140 can be controlled by the computer 110 to maintain the sample fluid at a predetermined temperature.

The sample tank 150 can contain a sample fluid. The sample tank can have a sample tank drain 152, a sample tank inlet, a sample tank outlet, and a sample tank vent 157, or combinations thereof.

The sample tank inlet can be in communication with an outlet of the first capillary tube 190. A first flow control valve 161 can be located between the outlet of the first capillary tube 190 and the sample tank inlet. The first flow control valve 161 can control the flow of fluid into the sample tank 150. The first flow control valve 161 can be manual or automated.

The sample tank outlet can be in communication with an inlet of the pump 160. A second flow control valve 162 can be disposed between the pump 160 and the sample tank outlet. The second flow control valve 162 can be manual or automated. The second flow control valve 162 can control the flow out of the sample tank outlet to the pump 160.

The reference fluid tank 194 can contain a reference fluid. The reference fluid tank 194 can include a reference fluid tank inlet, a reference fluid tank vent 195, a reference fluid tank outlet, a second plurality of sensors 198, a reference fluid tank drain 199, or combinations thereof.

The reference fluid tank outlet can be in communication with the pump 160. A third flow control device 163 can be located between the pump 160 and the fluid tank outlet. The third flow control device 163 can be configured to control flow out of the sample fluid outlet to the pump 160. The third flow control device 163 can be manual or automated.

The reference fluid tank inlet can be in communication with the outlet of the second capillary tube 192. A fourth flow control device 164 can be operatively disposed between the outlet of the second capillary tube 192 and the reference fluid tank inlet. The fourth flow control device 164 can be selectively operated to control flow into the reference tank 194.

The pump 160 can have an inlet in communication with the sample tank outlet and another inlet in communication with the reference tank outlet. The pump 160 can have an outlet in communication with an inlet of the first capillary tube 190 and another outlet in communication with the inlet of the second capillary tube 192.

The first pressure gauge 180 can be located between the inlet of the first capillary tube 190 and the outlet of the pump 160 in communication with the inlet of the first capillary tube 190. The first pressure gauge 180 can monitor the pressure of the sample fluid entering the first capillary tube 190, it can also be a differential pressure gauge across the capillary tube 190. The pressure gauge 180 can send signals to the data acquisition system 120. The data acquisition system 120 can transform the signals to data and acquire pressure data for the sample fluid entering the first capillary tube 190.

The second pressure gauge 182 can be in communication with the pump 160. The second pressure gauge 182 can send signals to the data acquisition system 120. The data acquisition system 120 can transform the signals to data and acquire data on the pressure of the pump 160.

The third pressure gauge 184 can be located between the outlet of the pump 160 that is in communication with the inlet of the second capillary tube 192. The pressure gauge 184 can also be a differential pressure gauge across the capillary tube 192. The third pressure gauge 184 can send signals to the data acquisition system 120, the data acquisition system 120 can transform the signals to data, thereby acquiring data on the pressure of the reference fluid entering the second capillary tube 192.

The controllable fluid flow regulator 170 can be in communication with the computer 110. The computer 110 can control the fluid supply 172 to maintain the pressure or flow rate of the pump 160 at a predetermined pressure or flow rate or both. The computer can use the acquired pressure data of the sample fluid, reference fluid, and the pump 160 to selectively control the controllable fluid flow regulator 170 to maintain a predetermined pressure or flow rate or both in the pump 160.

The second plurality of sensors 198 can send signals to the data acquisition system 120. The data acquisition system 120 can transform the signals to data, thereby acquiring data on the reference fluid. The second plurality of sensors 198 can include temperature sensors, density measurement devices, or combinations thereof.

Figure 2:
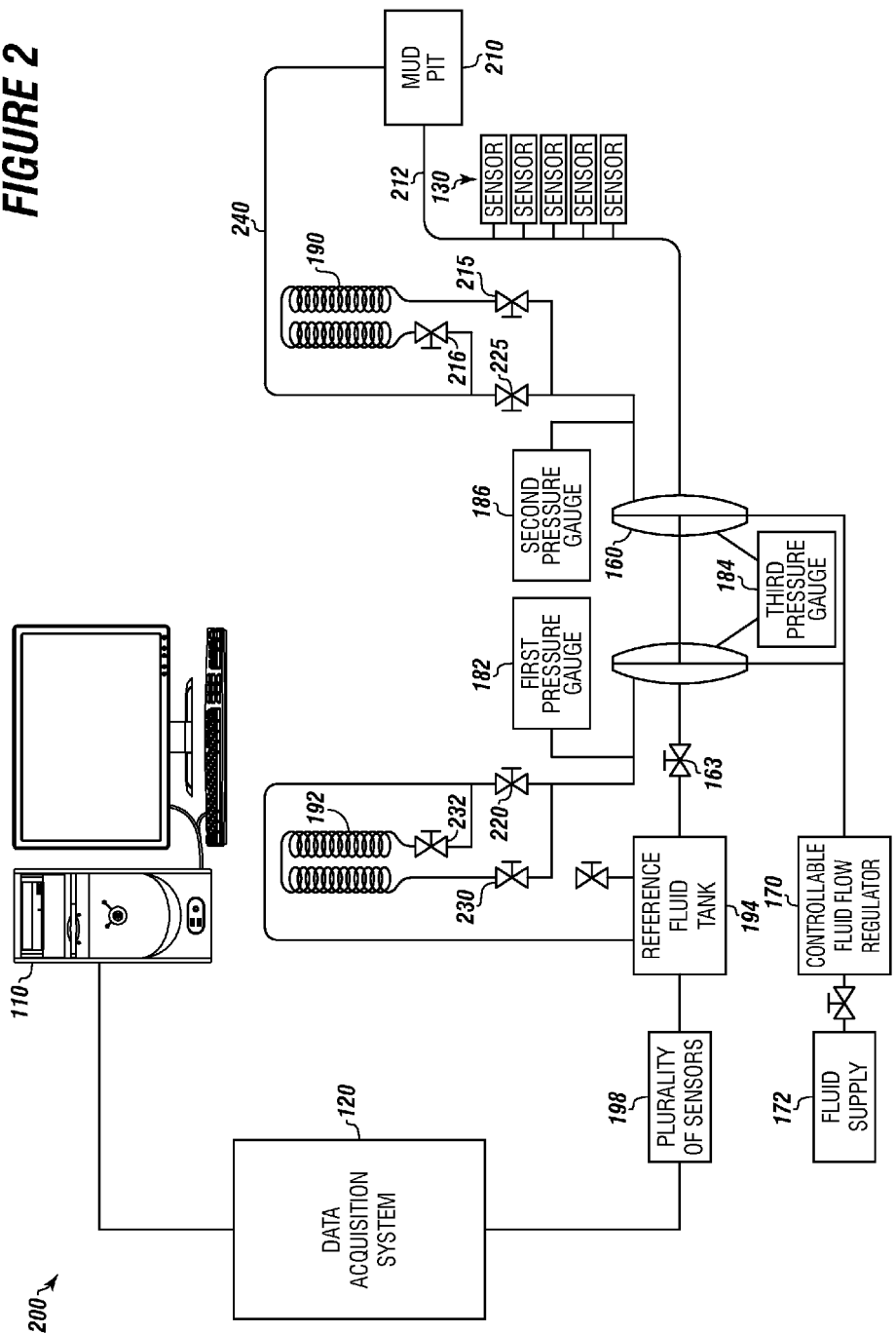
FIG. 2 depicts a schematic of the system when the sample fluid source is a mud pit.

FIG. 2 depicts a schematic of the system when the sample fluid source is a mud pit. The system 200 can include the computer 110, the data acquisition system 120, the reference fluid tank 194, the second plurality of sensors 198, the fluid supply 172, controllable fluid flow regulator 170, the pressure gauges 182, 184, and 186, the pump 160, the capillary tubes 190 and 192, and the first plurality of sensors 130.

The system 200 can operate substantially similar to the system 100. The system 200 can include a conduit 212 in communication with a mud pit 210 and an inlet of the pump 160. The first plurality of sensors can be in communication with the conduit 212. The third flow control device 163 can be selectively operated to control the flow of reference fluid out of the reference fluid tank outlet. A first bypass flow control device 220 can be operatively disposed in the system 200 to allow fluid out of the pump to bypass the second capillary tube 192, and a second bypass flow control device 225 can be operatively disposed in the system 200 to selectively allow fluid out of the pump 160 to bypass the first capillary tube 190.

A first measurement flow control device 230 can be operatively disposed in the system 200 to selectively allow fluid from the pump 160 to flow to the second capillary tube 192, and a second measurement flow control device 232 can be disposed in the system 200 to selectively allow fluid to flow out of the second capillary tube 192.

A third measurement flow control device 215 can be operatively disposed in the system to selectively control fluid flow into the first capillary tube 190, and a fourth measurement flow control device 216 can be operatively disposed in the system to selectively control fluid exiting the first capillary tube 190.

A return conduit 240 can be in fluid communication with the fourth measurement flow control device 216 and the second bypass flow control device 225 to allow sample fluid to be returned to the mud pit.

The system can be operated to allow purge of the system 200 using the sample fluid. The third flow control device 163 can be opened and the measurement flow control devices 230, 232, 216, and 215 can be closed. The bypass flow control valves 220 and 225 can be opened. The sample fluid can be pump from the mud pit 210 and flow through the second bypass flow control device 225 to the return conduit 240, and reference fluid can flow from the reference fluid tank 194 through the first bypass flow control device 220 back to the reference tank.

After purging the bypass flow control valves 220 and 225 can be closed, and the measurement flow control devices 232, 230, 215, and 216 can be opened. Fluid now can be pumped from the mud pit 210 via conduit 212 and pump 160 through the third measurement flow control device 215 through the first capillary tube 190 through the fourth measurement flow control device 216 to the return conduit 240 and back to the mud pit 210. At the same time reference fluid can be pump through the pump 160 through the second measurement flow control device 232 through the second capillary tube 192 through the second measurement flow control device 230 back to the reference tank 194.

Figure 3:
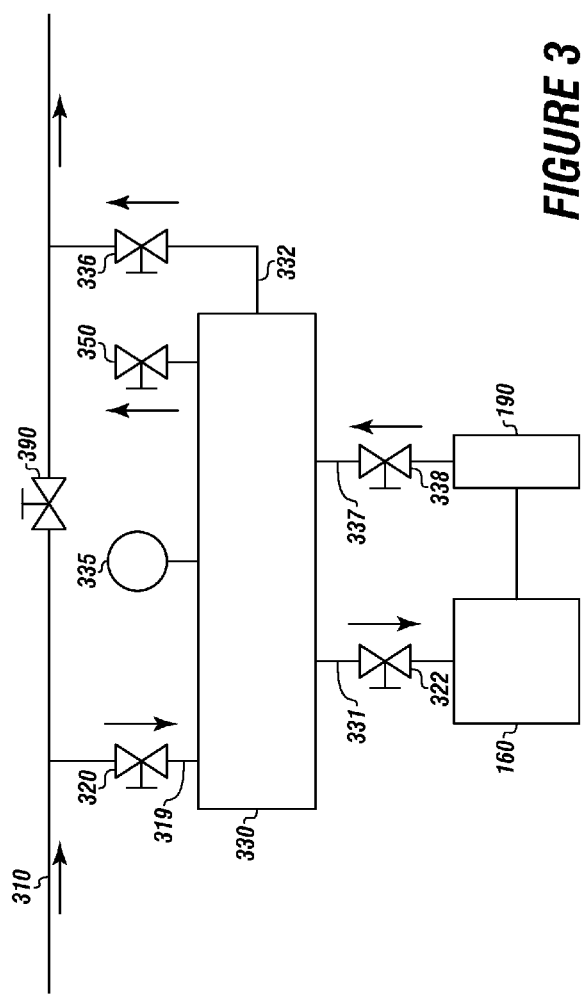
FIG. 3 depicts a schematic of a pressurized chamber that can be integrated into any of the systems described herein to provide a sample fluid from a pipeline.

FIG. 3 depicts a schematic of a pressurized chamber that can be integrated into any of the systems described herein to provide a sample fluid from a pipeline.

The pressurized chamber 330 can have a first inlet 319 with a first inlet flow control device 320 in communication therewith. The first inlet can be in fluid communication with a pipeline 310. The first inlet flow control device 320 can be selectively operated to allow sample fluid from the pipeline 310 to flow into the pressurized chamber 330.

The pressurized chamber 330 can have a first outlet 331. A first outlet flow control device 322 can be selectively operated to allow sample fluid to exit the pressurized chamber 330 and flow into the pipeline 310.

The pressurized chamber 330 can also include a second outlet 332 with a second outlet flow control device 336 in communication therewith. The second outlet flow control device 336 can be selectively operated to allow sample fluid to flow to the pump 160.

The pressurized chamber 330 can also include a second inlet 337. A second inlet flow control device 338 can be operatively connected thereto. The second inlet flow control device 338 can be selectively operated to allow sample fluid to flow into the pressurized chamber 330 from the first capillary tube 190.

A gauge 335 can be connected to the pressurized chamber 330. The gauge 335 can be used to monitor the pressure in the pressurized chamber 330. The monitoring can include displaying a measured pressure, sending a signal correlated with the pressure in the pressurized chamber 330 to the data acquisition system, or combinations thereof.

The pressurized chamber 330 can also include a bleed valve 350.

In operation, the sample fluid can be collected from the pipeline by closing the first outlet flow control device 322, the second outlet flow control device 336, and the second inlet flow control device 338. The first inlet flow control device 320 can be opened. As such fluid can flow from the pipeline 310 into the pressurized chamber 330 via the first inlet 319.

The bleed valve 350 can be operated to reduce pressure of the sample fluid in the pressurized chamber 330. When the sample fluid reaches a predetermined value the bleed valve can be closed, and the second outlet flow control device 336 and the second inlet flow control device 338 can be opened. As such, sample fluid can flow from the pressurized chamber to the pump 160 and through the first capillary tube 190 and back to the pressurized chamber 330.

The sample fluid can be returned to the pipeline 310 by closing the second outlet flow control device 336 and the second inlet flow control device 338, and opening the first inlet flow control device 320 and the first outlet flow control device 322. The upstream portion of the pipeline 310 can be selectively isolated from a downstream portion by a pipeline valve 390. The pipeline valve 390 can be selectively operated to aid in the return of the sample fluid to the pipeline 310 and collection of the sample fluid from the pipeline 310.

Figure 4:
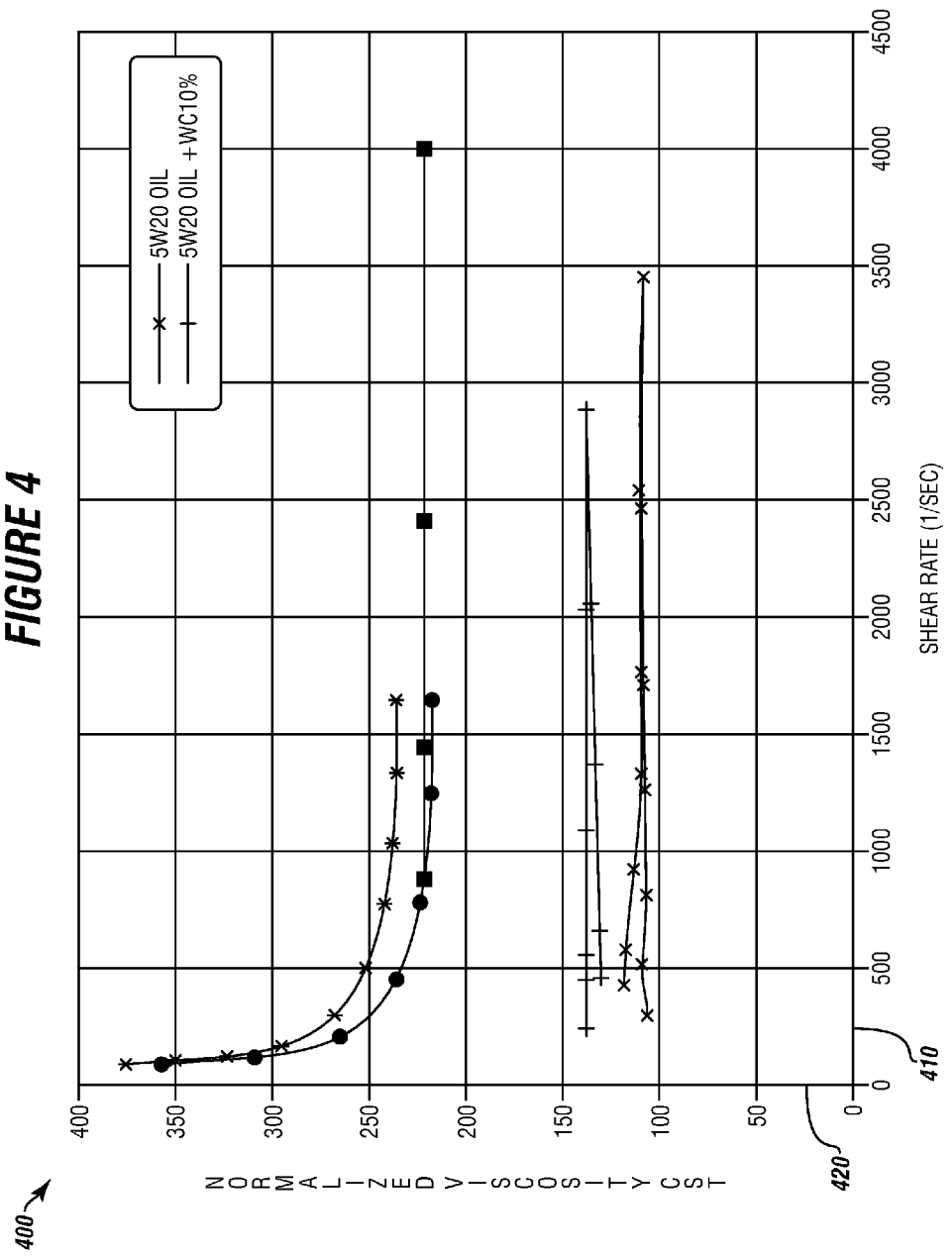
FIG. 4 depicts a graph of the measured Newtonian viscosity versus shear rate.

FIG. 4 depicts a graph of the measured Newtonian viscosity versus shear rate. The graph 400 can include an x-axis 410 and a y-axis 420. The x-axis 410 can be the shear rate and the y-axis 420 can be the normalized viscosity.

Figure 5:
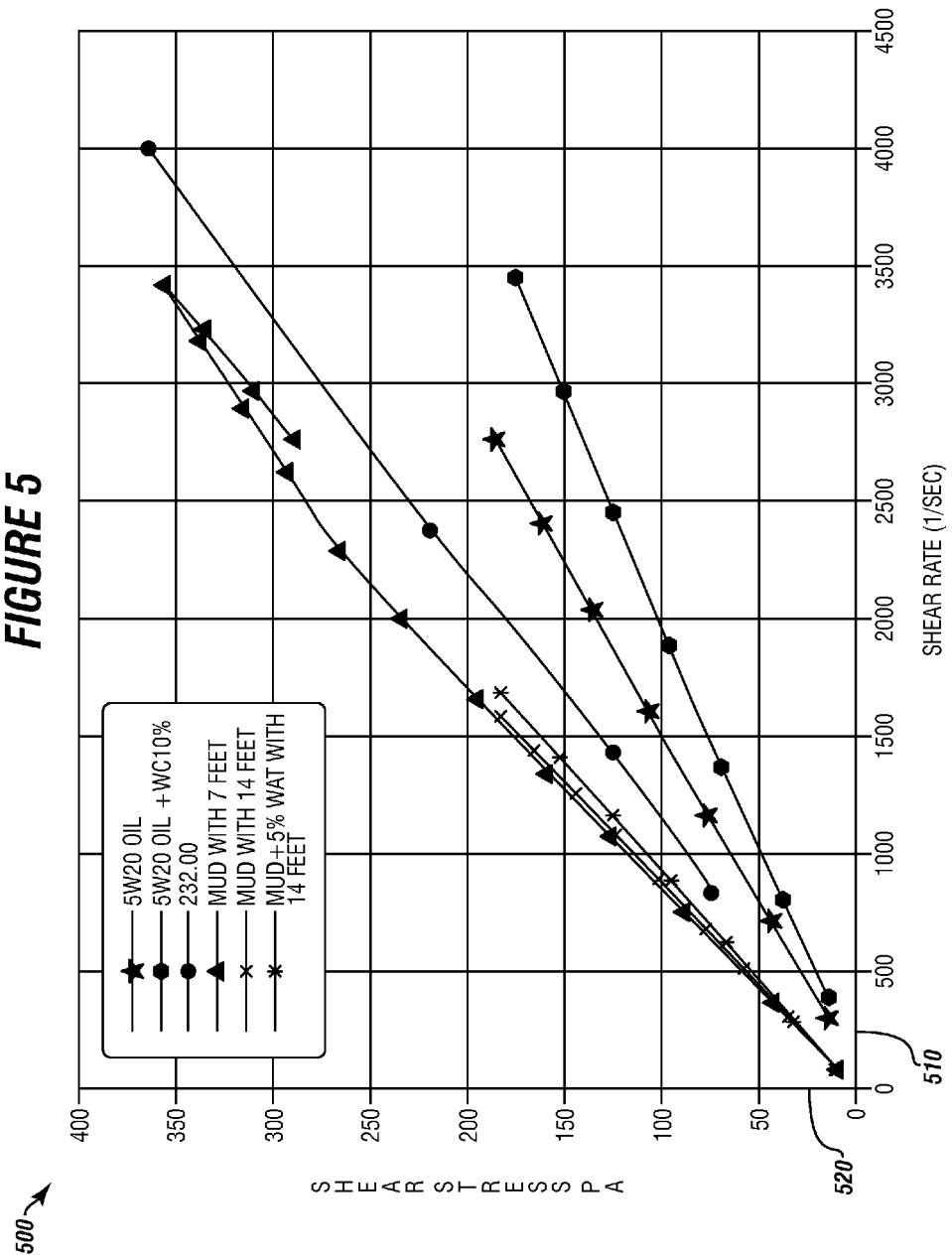
FIG. 5 depicts a Rheograph of a typical fluid test performed using the system.

FIG. 5 depicts a Rheograph of a typical fluid test performed using the system. The Rheograph 500 can include an x-axis 510 and a y-axis 520. The x-axis 510 can be the shear rate and the y-axis 520 can be the shear strength.

Figure 6:
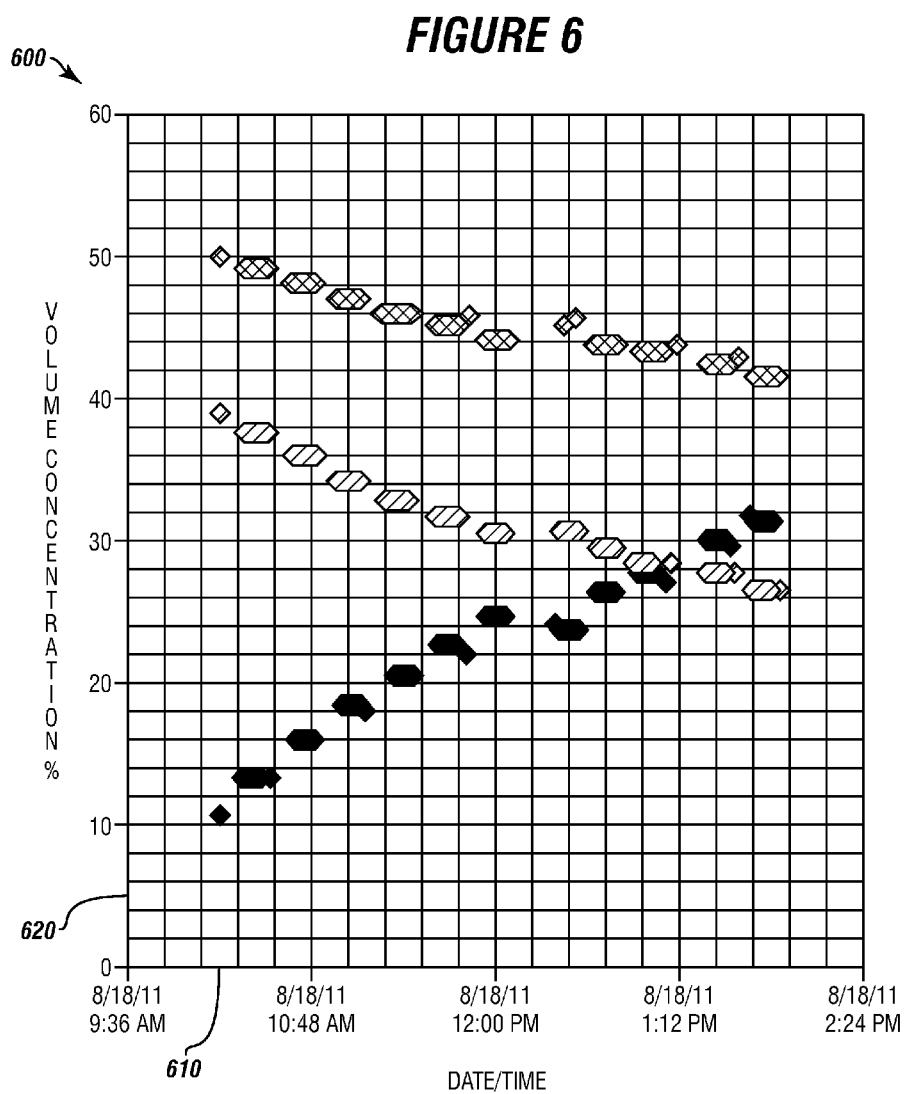
FIG. 6 depicts a graph of a drilling fluid volume concentration measured during gradual increase in water content.

FIG. 6 depicts a graph of a drilling fluid volume concentration measured during gradual increase in water content. The graph 600 can include an x-axis 610 and a y-axis 620. The x-axis 610 can represent value for the date and time that samples were measure, and the y-axis 620 can be the volume concentration percentage.

The system was utilized to test drilling fluid composition with drilling mud samples with changing volume concentrations of its basic ingredients: water, sand and oil, as it is shown in the FIG. 6.

It can be seen, that while water volume concentration is increasing, the volume concentrations of sand and oil are decreasing accordingly.

Figure 7:
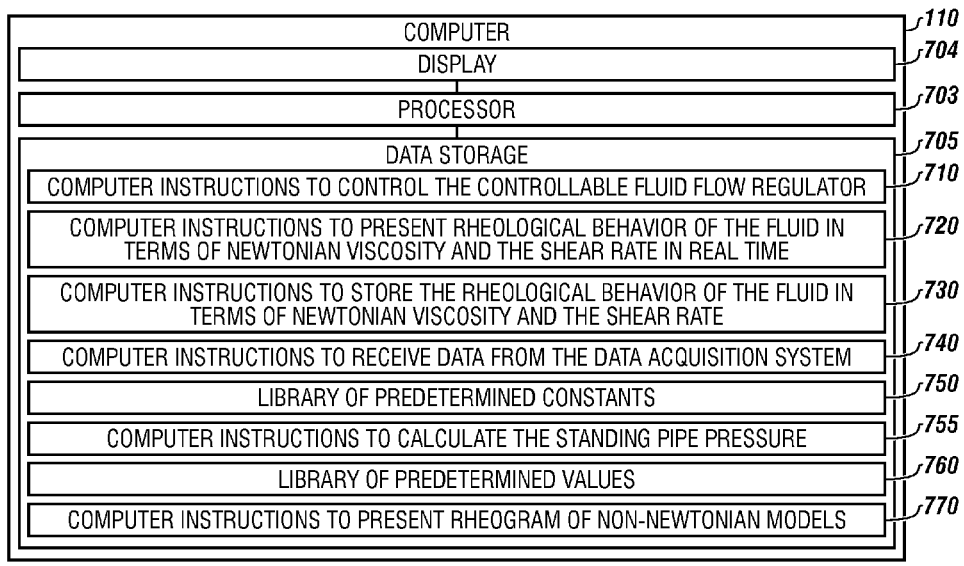
FIG. 7 depicts a schematic of a computer according to one or more embodiments.

FIG. 7 depicts a schematic of the computer 110 according to one or more embodiments.

The computer 110 can have a data storage 705. The computer can include a display 704 in communication with a processor 703. The processor 703 can be in communication with the data storage 705.

The data storage 705 can include computer instructions to control the controllable fluid flow regulator 710. The computer instructions to control the controllable fluid flow regulator 710 can used data acquired form the data acquisition system, such a pressure in the pump, pressure of the reference fluid, and pressure of the sample fluid and predetermined values for pressure stored in the library of predetermined values 760 to control the controllable fluid flow regulator. For example, the computer instructions to control the controllable fluid flow regulator 710 can compare the acquired pressure data to the predetermined values and increase or decrease the flow of fluid from the fluid supply into the pump by closing or opening the controllable fluid flow regulator.

The data storage 705 can include computer instructions to present rheological behavior of the fluid in terms of Newtonian viscosity and the shear rate in real time 720.

These computer instructions can have an algorithm for calculating $\mu_s = \mu_r (\tau_s p_s)/(\tau_r p_r)$ can be used. $\mu_s$ is the measurement viscosity of the sample fluid; $\mu r$ is the viscosity of the reference fluid; $\tau_s$ is the sample fluid stroke time; $p_s$ is the pressure at the outlet of the pump for the sample fluid; $\tau_r$ is the reference fluid stroke time; $p_r$ is the pressure at the outlet of the pump for the reference fluid. By accounting for both the stroke time of both fluids and the pressure of both fluids a more accurate viscosity can be calculated for the sample fluid.

These computer instructions can have an algorithm for calculating the shear rate using the following: $\gamma = 8v/D = 2Q*\pi*D \, V/\tau s$. $\gamma$ is the shear rate; $v$ is the velocity of the sample fluid through the capillary; D is the capillary diameter; Q is the flow rate; V is pump displacement; and $\tau s$ is the sample fluid stroke time. And the computer instructions can include algorithms to generate a graph of the Newtonian viscosity vs. the shear rate.

The data storage 705 can include computer instructions to store the rheological behavior of the fluid in terms of Newtonian viscosity and the shear rate 730. The computer instructions can store the graph and calculated shear rate for off-line analysis.

The data storage 705 can include computer instructions to receive data from the data acquisition system 740.

The data storage 705 can include a library of predetermined constants 750. The predetermined constants can include Bingham Plastic constant, Power Law Constant, Herschel-Bulkley constant Bingham Number, Blak Number, or combinations thereof.

The data storage 705 can include computer instructions to calculate the standing pipe pressure 755. The standing pipe pressure can be calculated using constants from the library of predetermined constants 750 and additional inputs of the pipe and drilling geometry.

The library of predetermined values 760 can include predetermined pressure values, predetermined sample fluid temperatures, other predetermined values, or combinations thereof.

The data storage 705 can include computer instructions to present Rheogram of non-Newtonian models 770. These computer instructions can include algorithms for calculating shear using t=PD/4L. t is the shear stress, P is the discharge pressure of the pump, and L is the length of the capillary tube.

The data storage 705 can include computer instructions to determine composition of multi component fluids using the dielectric method. These computer instructions can include algorithms for utilizing Landau-Lifshitz-Looyenga [LLL] mixing formula, as it is disclosed in the publication by Turner et al. [1990]. The LLL mixing formula can be easy expanded to the mixture of 3 and more components. The algorithm can utilize the following equations:

$$\in_m = a_o \in_o^b + a_s \in_s^b + a_w \in_w^b \quad \text{Equation 1:}$$

The density of the drilling fluid can be described by Equation 2: $\rho_m = a_o \rho_o + a_s \rho_s^b + a_w \rho_w$.

Equation 3 is the normalizing equation for volume fractions of the drilling fluid, and equation 3 can be represented as: $1 = a_o + a_s + a_w$. $\rho$—fluid density, $\in$—fluid dielectric constant, $a$—volume fraction of fluid in the mixture, $b$—power coefficient, usually $b=\frac{1}{3}$, but it may be adjusted to the specific fluids, the indexes designate: oil—[o], sand—[s], water—[w], mixture—[m].

The dielectric constants of oil, sand and water can be stored in the library of predetermined constants 750 in advance, or they can be measured using the plurality of sensors and the data acquisition system.

Equations (1), (2) and (3) can be used in order to calculate the drilling fluid component volume fractions, if the densities and dielectric constants of fluid components are known and the drilling fluid parameters: density d[m] and dielectric constant e[m] are simultaneously measured.

The solution for the volume fractions are as follows:

A. Water volume fraction—a[w]:

$$a_w = \frac{(\varepsilon_m^b - \varepsilon_s^b)(\rho_s - \rho_o) + (\varepsilon_s^b - \varepsilon_o^b)(\rho_s - \rho_m)}{(\varepsilon_w^b - \varepsilon_s^b)(\rho_s - \rho_o) + (\varepsilon_s^b - \varepsilon_o^b)(\rho_s - \rho_w)}$$

B. Solid phase [sand] volume fraction—a[s]:

$$a_s = \frac{(\varepsilon_m^b - \varepsilon_w^b)(\rho_o - \rho_w) - (\varepsilon_o^b - \varepsilon_w^b)(\rho_m - \rho_w)}{(\varepsilon_s^b - \varepsilon_w^b)(\rho_o - \rho_w) - (\varepsilon_o^b - \varepsilon_w^b)(\rho_w - \rho_s)}$$

C. Oil volume fraction—a[o]:

$$a_o = 1 - a_s - a_w$$

Figure 8:
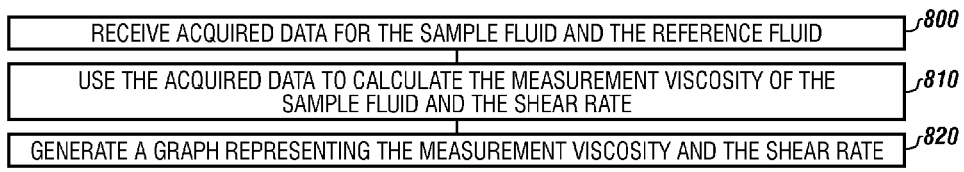
FIG. 8 depicts a logic loop executed by computer instruction for comparing data acquired for a sample fluid and a reference fluid, and computer instructions for presenting present rheological behavior of the sample fluid as Newtonian viscosity and the shear rate in real time.

FIG. 8 depicts a logic loop executed by the computer instruction for comparing the data acquired for the sample fluid and the reference fluid, and the computer instructions for presenting present rheological behavior of the sample fluid as Newtonian viscosity and the shear rate in real time.

At 800, the computer can receive acquired data for the sample fluid and the reference fluid.

At 810, the computer can use the acquired data to calculate the measurement viscosity of the sample fluid and the shear rate.

At 820, the computer can generate a graph representing the measurement viscosity and the shear rate.

Figure 9:
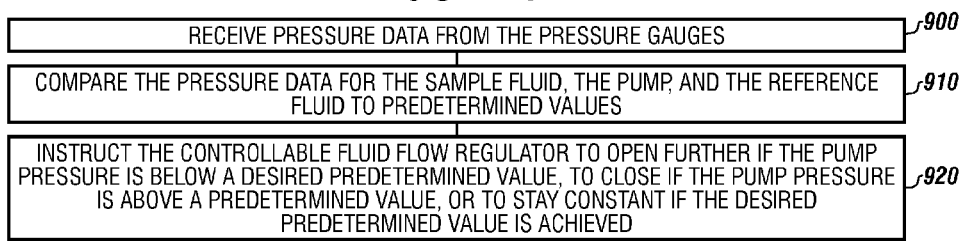
FIG. 9 depicts a logic loop followed by the computer instructions for controlling the controllable fluid flow regulator.

FIG. 9 depicts a logic loop followed by the computer instructions for controlling the controllable fluid flow regulator.

At 900, the computer can receive pressure data from the pressure gauges.

At 910, the computer can compare the pressure data for the sample fluid, the pump, and the reference fluid to predetermined values.

At 920, the computer can instruct the controllable pressure regulator to open further if the pump pressure is below a desired predetermined value, to close if the pump pressure is above a predetermined value, or to stay constant if the desired predetermined value is achieved.

While these embodiments have been described with emphasis on the embodiments, it should be understood that within the scope of the appended claims, the embodiments might be practiced other than as specifically described herein.

What is claimed is:

1. A system for on-line multi-component fluid analysis, wherein said system comprises:
   a first capillary tube in communication with a reference fluid source in a reference fluid flow path;
   a second capillary tube in fluid communication with a sample fluid source in a sample fluid flow path;
   a pump in fluid communication with said first capillary tube and said second capillary tube, said reference fluid flow path being in fluid isolation from said sample fluid flow path;
   a pump fluid supply in communication the pump;
   a controllable fluid flow regulator disposed between said pump fluid supply and said pump, wherein pumping action of pump fluid through said pump actuates reference fluid through said reference fluid flow path and sample fluid through said sample fluid flow path simultaneously;
   a first pressure gauge in said reference fluid flow path so as to collect data from said first capillary;
   a second pressure gauge in said sample fluid flow path so as to collect data from said second capillary;
   a data acquisition system in communication with said pump, said controllable fluid flow regulator, and first and second pressure gauges; and
   a computer in communication with said data acquisition system, wherein said computer controls said controllable fluid flow regulator so as to determine rheological behavior of the fluid in terms of Newtonian viscosity and shear rate in real time.

2. The system for on-line multi-component fluid analysis of claim 1, wherein said sample fluid is sourced from at least one of the group consisting of: a tank, a mud pit, and a pipeline.

3. The system of claim 2, wherein said sample fluid is sourced from said pipeline, said system further comprising:
   a pressure chamber in communication with a first portion of said pipeline via a first conduit, and in fluid communication with a second portion of said pipeline via a second conduit,
   wherein flow through said first conduit is controlled by a first flow valve and flow through said second conduit is controlled by a second flow valve, wherein said pressure chamber has a pressure relief valve releasing pressure from said sample fluid in said pressure chamber, and wherein said pressure chamber has an outlet in fluid communication with said sample fluid flow path.

4. The system of claim 1, wherein solids pass through the first and second capillary tubes.

5. The system of claim 1, wherein said pump is a self-priming pump.

6. The system for on-line multi-component fluid analysis of claim 1, further comprising a plurality of sensors in communication with said sample fluid flow path and said data acquisition system.

7. The system for on-line multi-component fluid analysis of claim 1, further comprising a temperature controller operatively connected to said sample fluid.

8. The system for on-line multi-component fluid analysis of claim 1, further comprising a purge system flushing the first and second capillary tubes with sample fluid prior to running measurements.

9. The system for on-line multi-component fluid analysis of claim 1, wherein said computer determines composition of said sample fluid.

10. The system for on-line multi-component fluid analysis, according to claim 1, wherein said rheological behavior is comprised of absolute viscosity, wherein said data from said first capillary tube is comprised of pressure at discharge of a set amount of reference fluid from said first capillary tube and amount of time for one cycle of said pump, and wherein said data from said second capillary tube is comprised of pressure at discharge of a set amount of sample fluid from said second capillary tube and said amount of time for one cycle of said pump simultaneous with discharge of said set amount of reference fluid.

11. The system for on-line multi-component fluid analysis of claim 10, wherein said data from said second capillary tube is comprised of property data according to said sample fluid.

12. The system for on-line multi-component fluid analysis of claim 11, wherein said property data is comprised of at least one of a group consisting of: composition of hydrocarbon, composition of solids, composition of water, salt content of said sample fluid, fluid density of said sample fluid, density of said sample fluid, temperature of said sample fluid, and electrical stability of said sample fluid.

13. A method for on-line multi-component fluid analysis with the system of claim 1, wherein the method comprises:

pumping said reference fluid through said first capillary tube in said reference fluid flow path using said pump;

pumping said sample fluid through said second capillary in said sample fluid flow path using said pump;

controlling said controllable fluid flow regulator while pumping the sample fluid and reference fluid through the first and second capillary tubes, respectively;

acquiring data from said first capillary tube by measuring time of one cycle of said pump and monitoring pressure at an outlet of said reference fluid;

acquiring data from said second capillary tube by measuring said time of one cycle of said pump and monitoring pressure at an outlet of said sample fluid;

comparing said data from said first capillary for said reference fluid to said data from said second capillary for said sample fluid; and determining and presenting Newtonian viscosity and shear rate in real time.

14. The method for on-line multi-component fluid analysis of claim 13, further comprising controlling temperature of said sample fluid.

15. The method of claim 13, further comprising:

connecting a first conduit with a pressure chamber and a first portion of a pressure pipeline;

connecting a second conduit with said pressure chamber and a second portion of said pressure pipeline;

connecting an outlet of said pressure chamber with said pump;

flowing through the first conduit and second conduit and preventing fluid flow out of said outlet to obtain a pressured fluid sample;

preventing fluid flow through said first conduit and said second conduit after said pressured fluid sample is collected in said pressure chamber;

reducing pressure of said pressured fluid sample in said pressure chamber to a predetermined pressure forming a fluid sample; and flowing said fluid sample to said pump and through said second capillary tube.

* * * * *